United States Patent
Kim et al.

(10) Patent No.: US 10,913,055 B2
(45) Date of Patent: *Feb. 9, 2021

(54) HYDROFORMYLATION CATALYST, COMPOSITION INCLUDING HYDROFORMYLATION CATALYST, AND METHOD OF PREPARING ALDEHYDE USING HYDROFORMYLATION CATALYST

(71) Applicant: LG CHEM, LTD., Seoul (KR)

(72) Inventors: Mi Young Kim, Daejeon (KR); Sung Shik Eom, Daejeon (KR); Dong Hyun Ko, Daejeon (KR); Da Won Jung, Daejeon (KR); Tae Yun Kim, Daejeon (KR); Min Ji Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 69 days.

This patent is subject to a terminal disclaimer.

(21) Appl. No.: 15/765,979

(22) PCT Filed: Jul. 4, 2017

(86) PCT No.: PCT/KR2017/007054
§ 371 (c)(1),
(2) Date: Apr. 4, 2018

(87) PCT Pub. No.: WO2018/008928
PCT Pub. Date: Jan. 11, 2018

(65) Prior Publication Data
US 2018/0290132 A1 Oct. 11, 2018

(30) Foreign Application Priority Data

Jul. 8, 2016 (KR) .................. 10-2016-0086766
Jun. 27, 2017 (KR) .................. 10-2017-0081085

(51) Int. Cl.
| | |
|---|---|
| *C07C 47/02* | (2006.01) |
| *B01J 31/18* | (2006.01) |
| *C07C 45/50* | (2006.01) |
| *C07C 45/62* | (2006.01) |
| *B01J 31/20* | (2006.01) |

(52) U.S. Cl.
CPC ............ *B01J 31/185* (2013.01); *B01J 31/20* (2013.01); *C07C 45/50* (2013.01); *C07C 45/62* (2013.01); *C07C 47/02* (2013.01); *B01J 2231/321* (2013.01); *B01J 2531/822* (2013.01); *B01J 2531/827* (2013.01); *B01J 2531/845* (2013.01)

(58) Field of Classification Search
None
See application file for complete search history.

(56) References Cited

U.S. PATENT DOCUMENTS 4,871,880 A * 10/1989 Omatsu ................... C07C 45/49
568/454

FOREIGN PATENT DOCUMENTS

| CN | 102803277 A | 11/2012 |
|---|---|---|
| CN | 103201036 A | 7/2013 |
| EP | 2 445 920 B1 | 3/2014 |
| KR | 2010019058 * | 2/2010 |
| KR | 10-1150557 B1 | 6/2012 |
| KR | 10-2015-0015904 A | 2/2015 |

OTHER PUBLICATIONS

Ryu et al. KR 2010019058, Machine-generated English translation (Year: 2010).*
Van Rooy et al., "Hydroformylation with a Rhodium/Bulky Phosphite Modified Catalyst. Catalyst Comparison for Oct-1-ene, Cyclohexene, and Styrene", Organometallics, 1995, vol. 14, No. 1, pp. 34-43.
Kubis et al., "A Comparative in Situ HP-FTIR Spectroscopic Study of Bi- and Monodentate Phosphite-Modified Hydroformylation", ChemCatChem, 2010, vol. 2, No. 3, pp. 287-295.
Selent et al., "A New Diphosphite Promoting Highly Regioselective Rhodium-Catalyzed Hydroformylation", Organometallics, 2011, vol. 30, No. 17, pp. 4509-4514.

* cited by examiner

*Primary Examiner* — Yun Qian
(74) *Attorney, Agent, or Firm* — Dentons US LLP

(57) ABSTRACT

A hydroformylation catalyst having excellent catalytic activity and stability, a composition including the hydroformylation catalyst, and a method of preparing an aldehyde using the hydroformylation catalyst, wherein, when hydroformylation of an olefin compound is performed in the presence of the hydroformylation catalyst to prepare an aldehyde, the normal/iso (n/i) ratio of the prepared aldehyde is lowered, and synthesis gas yield is increased.

11 Claims, No Drawings

HYDROFORMYLATION CATALYST, COMPOSITION INCLUDING HYDROFORMYLATION CATALYST, AND METHOD OF PREPARING ALDEHYDE USING HYDROFORMYLATION CATALYST

This application is a National Stage Application of International Application No. PCT/KR2017/007054 filed Jul. 4, 2017, and claims the benefit of Korean Patent Application No. 10-2016-0086766 filed Jul. 8, 2016 and Korean Patent Application No. 10-2017-0081085 filed Jun. 27, 2017, all of which are hereby incorporated by reference in their entirety for all purposes as if fully set forth herein.

CROSS-REFERENCE TO RELATED APPLICATIONS

This application claims priority to Korean Patent Application No. 10-2016-0086766, filed on Jul. 8, 2016, and Korean Patent Application No. 10-2017-0081085, filed on Jun. 27, 2017, in the Korea Intellectual Property Office, the disclosure of each of which is incorporated herein by reference.

TECHNICAL FIELD

The present disclosure relates to a hydroformylation catalyst, a composition including the hydroformylation catalyst, and a method of preparing an aldehyde using the hydroformylation catalyst, and more particularly, to a hydroformylation catalyst having excellent catalytic activity and stability, a composition including the hydroformylation catalyst, and a method of preparing an aldehyde using the hydroformylation catalyst, wherein, when hydroformylation of an olefin compound is performed in the presence of the hydroformylation catalyst to prepare an aldehyde, the normal/iso (n/i) ratio of the prepared aldehyde is lowered, and synthesis gas yield is increased.

BACKGROUND ART

A hydroformylation reaction, in which various olefins are reacted with carbon monoxide (CO) and hydrogen ($H_2$), commonly called synthesis gas, in the presence of a homogeneous organometallic catalyst and a ligand to prepare linear (normal) and branched (iso) aldehydes with one increase in carbon number, was first discovered in 1938 by Otto Roelen in Germany.

The hydroformylation reaction, also known as the OXO reaction, is industrially very important in homogeneous catalytic reactions. Various aldehydes including alcohol derivatives are prepared through the OXO reaction, and the prepared aldehydes are consumed worldwide.

Various aldehydes synthesized by the OXO reaction may be oxidized or hydrogenated after the condensation reaction of aldol or the like and transformed into various acids and alcohols containing long alkyl groups. In particular, alcohols obtained by hydrogenating aldehydes prepared by the OXO reaction are called oxo-alcohols. Oxo-alcohols are widely used industrially as solvents, additives, raw materials for various plasticizers, synthetic lubricating oils, and the like.

In this regard, since the value of linear aldehyde derivatives (normal-aldehydes) in aldehydes prepared by the OXO reaction has been high in the past, most studies on catalysts have focused on increasing the proportion of linear aldehyde derivatives. However, recently, demand for branched aldehyde derivatives (isoaldehydes) has increased due to the development of methods of preparing isobutyric acid, neopentyl glycol (NPG), 2,2,4-trimethyl-1,3-pentanediol, isovaleric acid, and the like using the isoaldehydes as raw materials, and research has focused on increasing the proportion of branched aldehyde derivatives. Therefore, it is necessary to develop a catalyst having excellent catalytic stability and activity while lowering a normal/iso (n/i) ratio.

PRIOR ART DOCUMENT

[Patent Document] KR 1150557 B1

DISCLOSURE

Technical Problem

Therefore, the present disclosure has been made in view of the above problems, and it is one object of the present disclosure to provide a hydroformylation catalyst having excellent catalytic activity and stability and a composition including the hydroformylation catalyst, wherein, when hydroformylation of an olefin compound is performed in the presence of the hydroformylation catalyst to prepare an aldehyde, the normal/iso (n/i) ratio of the prepared aldehyde is lowered.

It is another object of the present disclosure to provide a method of preparing an aldehyde using the hydroformylation catalyst.

The above objects and other objects of the present disclosure can be achieved by the present invention described below.

Technical Solution

In accordance with one aspect of the present disclosure, provided is a hydroformylation catalyst, including a phosphite ligand represented by Formula 1 below;
and

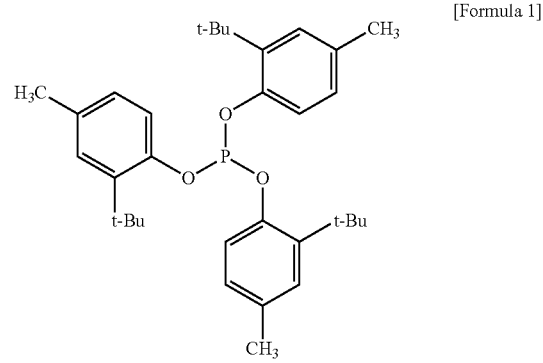

[Formula 1]

a transition metal compound represented by Formula 2 below,

[Formula 2]

(M is one selected from the group consisting of cobalt (Co), rhodium (Rh), iridium (Ir), ruthenium (Ru), iron (Fe), nickel (Ni), palladium (Pd), platinum (Pt), and osmium (Os); $L^1$, $L^2$, and $L^3$ are each independently one selected from the group consisting of hydrogen, a carbonyl (CO), cyclooctadiene, norbornene, chlorine, triphenylphosphine (TPP), and acetylacetonato (AcAc); x, y, and z are each independently 0 to 5; and x, y, and z are not at the same time), wherein the molar ratio of the phosphite ligand to the transition metal compound (L/M) is 24 to 390.

Preferably, the molar ratio of the phosphite ligand to the transition metal compound (L/M) is 24 to 237, 45 to 237, 47 to 237, 75 to 237, 79 to 237, 24 to 170, 24 to 160, 24 to 110, or 158 or less, or 119 or less. Within this range, the catalytic activity and stability of the hydroformylation catalyst are excellent, the normal/iso ratio of the prepared aldehyde is lowered, and synthesis gas yield is increased.

For example, based on 1 mole of the phosphite ligand represented by Formula 1, the transition metal compound represented by Formula 2 may be 0.003 to 0.05 mole, 0.004 to 0.045 mole, or 0.0042 to 0.0420 mole. Within this range, there is an advantage that catalyst activity is excellent.

For example, the transition metal compound represented by Formula 2 may be one or more selected from the group consisting of dicobalt octacarbonyl [$Co_2(CO)_8$], (acetylacetonato)dicarbonylrhodium [Rh(AcAc)(CO)$_2$], (acetylacetonato)carbonyl(triphenylphosphine)rhodium [Rh(AcAc)(CO)(TPP)], hydridocarbonyltris(triphenylphosphine)rhodium [HRh(CO)(TPP)$_3$], (acetylacetonato)dicarbonyliridium [Ir(AcAc)(CO)$_2$], and hydridocarbonyltris(triphenylphosphine)iridium [HIr(CO)(TPP)$_3$].

For example, the hydroformylation catalyst may catalyze hydroformylation of propylene to butyraldehyde.

For example, the molar ratio of n-butyraldehyde to isobutyraldehyde in the butyraldehyde prepared by catalysis of the hydroformylation catalyst may be 2 or less, less than 2, greater than 0 and less than 2, 1 or more and less than 2, 1 to 1.9, 1 to 1.7, 1 to 1.6, 1 to 1.5, 1 to 1.45, 1 to 1.4, 1 to 1.35, 1 to 1.3, 1 to 1.25 or 1 to 1.2. In this case, isobutyraldehyde may be generated in a high yield.

In accordance with another aspect of the present disclosure, provided is a hydroformylation catalyst composition, including 2 to 10% by weight of a phosphite ligand represented by Formula 1 below;

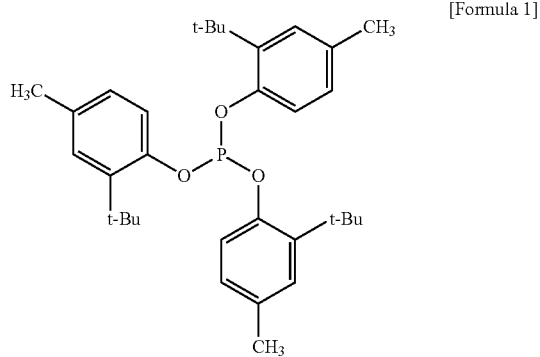

[Formula 1]

90 to 98% by weight of a solvent; and 40 to 390 ppm (based on transition metal) of a transition metal compound represented by Formula 2 below per the total weight of the hydroformylation catalyst composition,

[Formula 2]

wherein M is one selected from the group consisting of cobalt (Co), rhodium (Rh), iridium (Ir), ruthenium (Ru), iron (Fe), nickel (Ni), palladium (Pd), platinum (Pt), and osmium (Os); $L^1$, $L^2$, and $L^3$ are each independently one selected from the group consisting of hydrogen, a carbonyl (CO), cyclooctadiene, norbornene, chlorine, triphenylphosphine (TPP), and acetylacetonato (AcAc); x, y, and z are each independently 0 to 5; and x, y, and z are not at the same time.

For example, the amount of the transition metal compound may be 50 to 250 ppm, 75 to 250 ppm, or 50 to 200 ppm. Within this range, the catalytic activity and stability of the hydroformylation catalyst are excellent, the normal/iso ratio of the prepared aldehyde is lowered, and synthesis gas yield is increased. More preferably, the amount of the transition metal compound is 50 to 150 ppm, 50 to 95 ppm, 40 to 95 ppm, 40 to 80 ppm, 50 to 80 ppm, or 50 to 75 ppm. In this case, in addition to the above-mentioned advantages, it is possible to provide an economic advantage by using a small amount of the expensive transition metal compound.

The phosphite ligand is preferably contained in an amount of 3 to 9% by weight, 3 to 7% by weight, or 3 to 6% by weight, more preferably, 5 to 7% by weight or 5 to 6% by weight. Based on the amount of the phosphite ligand, the solvent is preferably contained in an amount of 91 to 97% by weight, 93 to 97% by weight, or 94 to 97% by weight, more preferably, 93 to 95% by weight or 94 to 95% by weight. In this case, the stability and activity of the hydroformylation catalyst are excellent, the normal/iso ratio of the prepared aldehyde is lowered, and synthesis gas yield is increased.

For example, the solvent may be one or more selected from the group consisting of propyl aldehyde, butyraldehyde, pentyl aldehyde, valeraldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane, and is preferably one or more selected from butyraldehyde and valeraldehyde. In this case, products obtained in the hydroformylation reaction may be easily purified, and side reaction may be minimized during the hydroformylation reaction.

In accordance with yet another aspect of the present disclosure, provided is a method of preparing an aldehyde, including a hydroformylation step of reacting an olefin with synthesis gas in the presence of the hydroformylation catalyst to prepare an aldehyde, wherein the synthesis gas includes carbon monoxide and hydrogen.

For example, the molar ratio of the carbon monoxide to the hydrogen may be from 5:95 to 70:30, from 40:60 to 60:40, or from 45:55 to 55:45. Within this range, the gas used for reaction is not accumulated in a reactor, and reaction balance may be excellent.

For example, the hydroformylation step may be performed at a reaction temperature of 50 to 90° C. or 60 to 90° C. and a reaction pressure of 5 to 25 bar or 8 to 18 bar.

As another example, the hydroformylation step may be performed at a reaction temperature of 70 to 90° C. or 80 to 90° C. and a reaction pressure of 5 to 13 bar, 7 to 13 bar, 7 to 12 bar, 8 to 12 bar, or 7 to 8 bar.

As another example, the hydroformylation step may be performed at a reaction temperature of 70 to 90° C. and a reaction pressure of 14 to 20 bar, 14 to 18 bar, 15 to 18 bar, or 14 to 15 bar.

At the reaction temperature and reaction pressure in the above range, the stability and activity of the catalyst are excellent, reaction may quickly proceed, and side reactions such as ligand decomposition may be minimized.

For example, the olefin may be propylene, and the aldehyde may be butyraldehyde.

For example, the molar ratio of n-butyraldehyde to isobutyraldehyde in the butyraldehyde may be 2 or less, less than 2, less than 2 and greater than 0, less than 2 and 1 or more, 1 to 1.9, 1 to 1.7, 1 to 1.6, 1 to 1.5, 1 to 1.45, 1 to 1.4, 1 to 1.35, 1 to 1.3, 1 to 1.25, or 1 to 1.2.

For example, synthesis gas yield (syn gas yield) in the hydroformylation step may be 80% by weight or more, 83% by weight or more, 85% by weight or more, 86% by weight or more, 88% by weight or more, or 88.5% by weight or more.

Advantageous Effects

As apparent from the foregoing, the present disclosure advantageously provides a hydroformylation catalyst having excellent catalytic activity and stability, a composition including the hydroformylation catalyst, and a method of preparing an aldehyde using the hydroformylation catalyst. According to the present disclosure, when hydroformylation of an olefin compound is performed in the presence of the hydroformylation catalyst to prepare an aldehyde, the normal/iso (n/i) ratio of the prepared aldehyde can be lowered.

BEST MODE

Hereinafter, the present disclosure will be described in detail.

When hydroformylation of an olefin is performed in the presence of a hydroformylation catalyst including a specified content of a particular phosphite ligand based on the content of a transition metal, preferably at a reaction temperature and a reaction pressure within a predetermined range, the normal/iso (n/i) ratio of an aldehyde was significantly lowered, synthesis gas yield was increased, and the catalytic activity and stability of the hydroformylation catalyst were found to be excellent. The present inventors confirmed the above results and completed the present invention on the basis thereof.

The hydroformylation catalyst according to the present disclosure, a composition including the hydroformylation catalyst, and a method of preparing an aldehyde using the hydroformylation catalyst are as follows.

The hydroformylation catalyst of the present disclosure includes a phosphite ligand represented by Formula 1 below; and

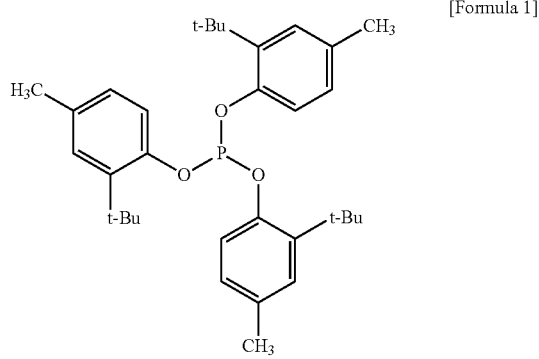

[Formula 1]

a transition metal compound represented by Formula 2 below,

[Formula 2]

(M is one selected from the group consisting of cobalt (Co), rhodium (Rh), iridium (Ir), ruthenium (Ru), iron (Fe), nickel (Ni), palladium (Pd), platinum (Pt), and osmium (Os); $L^1$, $L^2$, and $L^3$ are each independently one selected from the group consisting of hydrogen, a carbonyl (CO), cyclooctadiene, norbornene, chlorine, triphenylphosphine (TPP), and acetylacetonato (AcAc); x, y, and z are each independently 0 to 5; and x, y, and z are not 0 at the same time) wherein the molar ratio of the phosphite ligand to the transition metal compound (L/M) is 24 to 390. Within this range, isobutyraldehyde selectivity, synthesis gas yield (syn gas yield), and the catalytic activity and stability of the hydroformylation catalyst are all excellent.

The molar ratio of the phosphite ligand to the transition metal compound (L/M) is preferably 24 to 237, 45 to 237, 47 to 237, 75 to 237, 79 to 237, 24 to 170, 24 to 160, 24 to 110, or 158 or less, or 119 or less. Within this range, the catalytic activity and stability of the hydroformylation catalyst are excellent, and isobutyraldehyde selectivity and synthesis gas yield (syn gas yield) are increased.

For example, based on 1 mole of the phosphite ligand represented by Formula 1, the transition metal compound represented by Formula 2 may be contained in an amount of 0.003 to 0.05 mole, 0.004 to 0.045 mol, or 0.0042 to 0.0420 mol. Within this range, catalyst activity, isobutyraldehyde selectivity, and synthesis gas yield (syn gas yield) are increased.

For example, the transition metal compound represented by Formula 2 may be one or more selected from the group consisting of dicobalt octacarbonyl $[Co_2(CO)_8]$, (acetylacetonato)dicarbonylrhodium $[Rh(AcAc)(CO)_2]$, (acetylacetonato)carbonyl(triphenylphosphine)rhodium $[Rh(AcAc)(CO)(TPP)]$, hydridocarbonyltris(triphenylphosphine)rhodium $[HRh(CO)(TPP)_3]$, (acetylacetonato)dicarbonyliridium $[Ir(AcAc)(CO)_2]$, and hydridocarbonyltris(triphenylphosphine)iridium $[HIr(CO)(TPP)_3]$. In this case, the catalytic activity of the hydroformylation catalyst is excellent.

For example, the hydroformylation catalyst may catalyze hydroformylation of propylene to butyraldehyde. In this case, isobutyraldehyde selectivity and synthesis gas yield (syn gas yield) are increased.

For example, the molar ratio of n-butyraldehyde to isobutyraldehyde in the butyraldehyde prepared by catalysis of the hydroformylation catalyst may be 2 or less, less than 2, greater than 0 and less than 2, 1 or more and less than 2, 1 to 1.9, 1 to 1.7, 1 to 1.6, 1 to 1.5, 1 to 1.45, 1 to 1.4, 1 to 1.35, 1 to 1.3, 1 to 1.25, or 1 to 1.2. In this case, isobutyraldehyde may be generated in a high yield.

In addition, the hydroformylation catalyst composition of the present disclosure includes 2 to 10% by weight of a phosphite ligand represented by Formula 1 below;

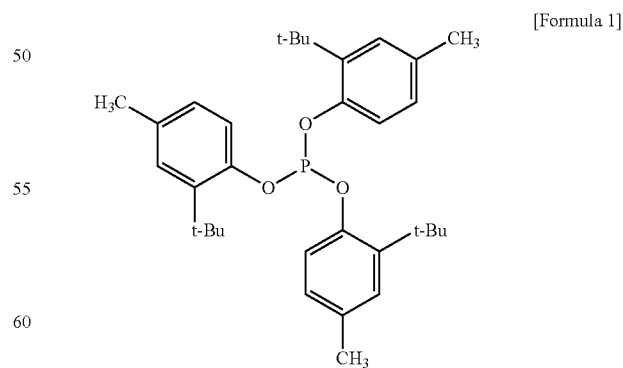

[Formula 1]

90 to 98% by weight of a solvent; and 40 to 390 ppm of a transition metal compound represented by Formula 2 below per the total weight of the hydroformylation catalyst composition, $$M(L^1)_x(L^2)_y(L^3)_z \quad \text{[Formula 2]}$$

wherein, M is one selected from the group consisting of cobalt (Co), rhodium (Rh), iridium (Ir), ruthenium (Ru), iron (Fe), nickel (Ni), palladium (Pd), platinum (Pt), and osmium (Os); $L^1$, $L^2$, and $L^3$ are each independently one selected from the group consisting of hydrogen, a carbonyl (CO), cyclooctadiene, norbornene, chlorine, triphenylphosphine (TPP), and acetylacetonato (AcAc); x, y, and z are each independently 0 to 5; and x, y, and z are not 0 at the same time. In this case, isobutyraldehyde selectivity, synthesis gas yield (syn gas yield), the catalytic activity and stability of the hydroformylation catalyst are all excellent. In addition, content analysis and reactivity confirmation are easy within the composition ratio, and problems associated with solubility such as ligand precipitation do not occur.

For example, the amount of the transition metal compound may be 50 to 250 ppm, 75 to 250 ppm, or 50 to 200 ppm. Within this range, the catalytic activity and stability of the hydroformylation catalyst are excellent, the normal/iso ratio of the prepared aldehyde is lowered, and synthesis gas yield is increased.

More preferably, the amount of the transition metal compound is 50 to 150 ppm, 50 to 95 ppm, 40 to 95 ppm, 40 to 80 ppm, 50 to 80 ppm, or 50 to 75 ppm. In this case, in addition to the above-mentioned advantages, it is possible to provide an economic advantage by using a small amount of the expensive transition metal compound.

The amount of the phosphite ligand is preferably 3 to 9% by weight, 3 to 7% by weight, or 3 to 6% by weight, more preferably, 5 to 7% by weight or 5 to 6% by weight, and based on the amount of the phosphite ligand, the amount of the solvent is preferably 91 to 97% by weight, 93 to 97% by weight, or 94 to 97% by weight, more preferably, 93 to 95% by weight or 94 to 95% by weight. Within this range, the normal/iso (n/i) ratio of an aldehyde is lowered, the activity and stability of the catalyst are excellent, and a reaction rate is excellent.

For example, the solvent may be one or more selected from the group consisting of propyl aldehyde, butyraldehyde, pentyl aldehyde, valeraldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane. In this case, the activity and stability of the catalyst are excellent.

More preferably, the solvent is preferably one or more selected from butyraldehyde and valeraldehyde. In this case, in addition to the above-mentioned advantages, products obtained in the hydroformylation may be easily purified, and side reaction may be minimized during the hydroformylation.

For example, when the catalyst composition includes a triphenylphosphine compound, the catalytic activity of the catalyst composition may be 300% or more, 500% or more, 500 to 1,000%, 550 to 1,000%, or 600 to 1,000%. Within this range, the catalytic activity is excellent.

For example, after the catalyst composition is inactivated at a temperature of 90° C. or higher, 90 to 150° C., or 100 to 120° C. for 15 hours, based on the gas consumption of the catalyst composition including the triphenylphosphine compound, the catalytic stability of the catalyst composition may be 100% or more, 100 to 600%, 100 to 550%, 200 to 550%, 250 to 550%, 300 to 550%, 350 to 550%, or 500% or more. Within this range, catalytic stability is excellent.

In addition, the method of preparing an aldehyde according to the present disclosure includes a hydroformylation step of reacting an olefin with synthesis gas in the presence of the hydroformylation catalyst to prepare an aldehyde, wherein the synthesis gas includes carbon monoxide and hydrogen. In this case, isobutyraldehyde selectivity, synthesis gas yield (syn gas yield), the catalytic activity and stability of the hydroformylation catalyst are all excellent.

For example, the hydroformylation step may be performed at a reaction temperature of 50 to 90° C. or 60 to 90° C. and a reaction pressure of 5 to 25 bar or 8 to 18 bar. Within this range, the normal/iso (n/i) ratio of an aldehyde is lowered, and the activity and stability of the catalyst are excellent.

As another example, the hydroformylation step may be performed at a reaction temperature of 70 to 90° C. or 80 to 90° C. and a reaction pressure of 5 to 13 bar, 7 to 13 bar, 7 to 12 bar, 8 to 12 bar, or 7 to 8 bar. Within this range, the normal/iso (n/i) ratio of an aldehyde is lowered, and the activity and stability of the catalyst are excellent.

As another example, the hydroformylation step may be performed at a reaction temperature of 70 to 90° C. and a reaction pressure of 14 to 20 bar, 14 to 18 bar, 15 to 18 bar, or 14 to 15 bar. Within this range, the normal/iso (n/i) ratio of an aldehyde is lowered, and the activity and stability of the catalyst are excellent.

For example, the olefin compound may be a compound represented by Formula 3 below.

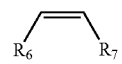

[Formula 3]

In Formula 3, for example, $R_6$ and $R_7$ may be each independently hydrogen, an alkyl group having 1 to 20 carbon atoms, fluorine (F), chlorine (Cl), bromine (Br), a trifluoromethyl group (—CF$_3$), or an aryl group having 0 to 5 substituents and having 6 to 20 carbon atoms. For example, the aryl group may be nitro (—NO$_2$), fluorine (F), chlorine (Cl), bromine (Br), methyl, ethyl, propyl, or butyl.

As a specific example, the olefin compound may be one or more selected from the group consisting of ethene, propene, 1-butene, 1-pentene, 1-hexene, 1-octene, and styrene.

As another example, the olefin may be propylene, and the aldehyde may be butyraldehyde. In this case, isobutyraldehyde selectivity and synthesis gas yield (syn gas yield) are increased.

For example, the molar ratio of n-butyraldehyde to isobutyraldehyde in the butyraldehyde may be 2 or less, less than 2, less than 2 and greater than 0, less than 2 and 1 or more, 1 to 1.9, 1 to 1.7, 1 to 1.6, 1 to 1.5, 1 to 1.45, 1 to 1.4, 1 to 1.35, 1 to 1.3, 1 to 1.25, or 1 to 1.2.

For example, synthesis gas yield (syn gas yield) in the hydroformylation step may be 80% by weight or more, 83% by weight or more, 85% by weight or more, 86% by weight or more, 88% by weight or more, or 88.5% by weight or more.

The hydroformylation of the olefin compound, according to the present disclosure, that is, a method of preparing an aldehyde may be represented by Reaction Formula 1 below.

[Reaction Formula 1]

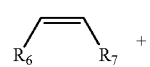 +

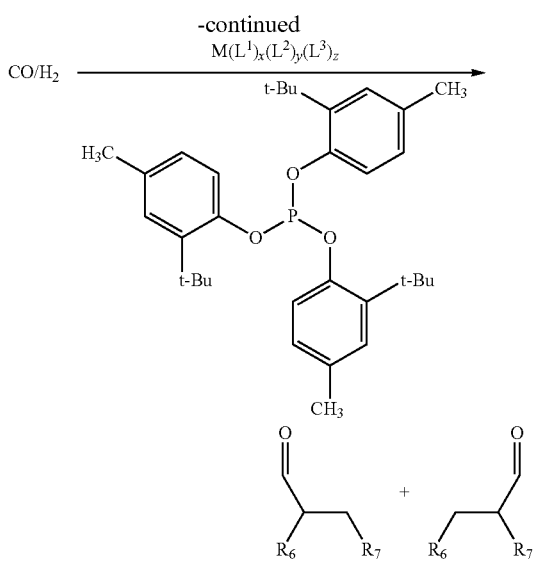

As a specific example, the transition metal compound represented by Formula 2 and the phosphite ligand represented by Formula 1 are dissolved in the solvent to prepare a mixed solution, that is, a catalyst composition containing the transition metal compound and the phosphite ligand. Then, the olefin compound represented by Formula 3 and synthesis gas ($CO/H_2$) are introduced into a conventional reactor together with the catalyst composition, and hydroformylation may be performed under elevated temperature and pressure while stirring the mixture to prepare an aldehyde.

The mixing ratio of carbon monoxide to hydrogen in the synthesis gas ($CO/H_2$) may be from 5:95 to 70:30, from 40:60 to 60:40, or from 45:55 to 55:45 on a molar basis. Within this range, gas used for reaction is not accumulated in the reactor and the reactivity of the catalyst is excellent.

Hereinafter, the present disclosure will be described in more detail with reference to the following preferred examples. However, these examples are provided for illustrative purposes only and should not be construed as limiting the scope and spirit of the present disclosure. In addition, it will be apparent to those skilled in the art that various changes and modifications may be made without departing from the spirit and scope of the present disclosure, and such changes and modifications are also within the scope of the appended claims.

EXAMPLE

Control Example 0.12 g (0.3 mmol) of (acetylacetonato)carbonyl(triphenylphosphine)rhodium (Rh (AcAc) (CO) (TPP), ROPAC) as a catalyst and a triphenylphosphine (TPP) compound were dissolved in a valeraldehyde solvent to prepare 100 g of a total solution (250 ppm of Rh, 6% by weight of TTP), and the solution was introduced into an autoclave reactor having a capacity of 600 ml. Then, propylene and synthesis gas ($CO/H_2$) were introduced into the reaction solution and reacted for 1 hour while stirring at the reaction pressure and reaction temperature shown in Table 1 below.

Examples 1 to 12, Comparative Examples 1 to 5, and Reference Examples 1 and 2

Instead of the triphenylphosphine (TPP) compound of Control Example, the phosphite and phosphine compounds shown in Table 1 below were added in an amount of weight % as a ligand, and reaction was performed in the same manner as in Control Example except that the reaction was performed at the reaction pressure and the reaction temperature shown in Tables 1 and 2 below.

Measurement Method

The normal/iso (n/i) ratio of an aldehyde was calculated by dividing the amount of prepared normal-butyraldehyde by the amount of prepared isobutyraldehyde, and the amount of each aldehyde was determined by gas chromatography (GC) analysis after reaction.

Syn gas yield: yield of prepared butyraldehyde versus input syn gas ($H_2$, CO).

TABLE 1

| Classification | Ligand (L) | Transition metal compound (Amount of transition metal) | Ligand content (% by weight) | L/Rh (mol/mol) | Reaction temperature (° C.) | Reaction pressure (bar) | n/i-BAL ratio | Syn gas yield (%) |
|---|---|---|---|---|---|---|---|---|
| Control Example | TPP | ROPAC (Rh 250 ppm) | 6 | 94 | 90 | 18 | 9.1 | 90.5 |
| | | | | | 80 | | 6.7 | 90.1 |
| | | | | | <80 | | — | 7.5 |
| Example 1 | TTBMPP | ROPAC (Rh 50 ppm) | 3 | 119 | 80 | 15 | 1.35 | 88.9 |
| | | | | | | 12 | 1.23 | 86.0 |
| | | | | | | 9 | 1.19 | 83.9 |
| | | | | | | 6 | 1.22 | 52.8 |
| | | | | | 90 | 18 | 1.26 | 88.5 |
| | | | | | 80 | | 1.42 | 88.2 |
| | | | | | 70 | | 1.69 | 87.9 |
| | | | | | 60 | | 2.03 | 87.7 |
| | | | | | 55 | | 2.14 | 15.3 |
| Example 2 | TTBMPP | ROPAC (Rh 250 ppm) | 6 | 47 | 90 | 8 | 1.24 | 88.2 |
| | | | | | 80 | | 1.43 | 88.3 |
| | | | | | 70 | | 1.77 | 88.2 |
| | | | | | 60 | | 2.15 | 86.0 |
| | | | | | 50 | | 2.25 | 87.5 |
| | | | | | <50 | | — | 12.4 |
| Example 3 | TTBMPP | ROPAC (Rh 250 ppm) | 6 | 47 | 90 | 18 | 1.54 | 88.2 |
| | | | | | 80 | | 1.75 | 85.9 |
| | | | | | 70 | | 1.91 | 88.2 |

TABLE 1-continued

| Classification | Ligand (L) | Transition metal compound (Amount of transition metal) | Ligand content (% by weight) | L/Rh (mol/mol) | Reaction temperature (° C.) | Reaction pressure (bar) | n/i-BAL ratio | Syn gas yield (%) |
|---|---|---|---|---|---|---|---|---|
| Example 4 | TTBMPP | ROPAC (Rh 250 ppm) | 3 | 24 | 90 | 18 | 1.09 | 90.6 |
| | | | | | 80 | | 1.13 | 89.6 |
| | | | | | 70 | | 1.35 | 87.8 |
| | | | | | 60 | | 1.57 | 87.1 |
| | | | | | 50 | | 1.80 | 42.5 |
| | | | | | <50 | | — | 8.9 |
| Example 5 | TTBMPP | ROPAC (Rh 75 ppm) | 3 | 79 | 80 | 18 | 1.25 | 90.3 |
| Example 6 | TTBMPP | ROPAC (Rh 75 ppm) | 6 | 158 | 80 | 18 | 1.17 | 89.2 |
| Example 7 | TTBMPP | ROPAC (Rh 75 ppm) | 9 | 237 | 80 | 18 | 1.44 | 90.8 |
| Example 8 | TTBMPP | ROPAC (Rh 50 ppm) | 6 | 238 | 80 | 18 | 1.63 | 89.1 |
| | | | | | 70 | | 1.81 | 88.1 |
| Example 9 | TTBMPP | ROPAC (Rh 50 ppm) | 4.5 | 179 | 80 | 18 | 1.60 | 88.9 |
| Example 10 | TTBMPP | ROPAC (Rh 50 ppm) | 7.5 | 297 | 80 | 18 | 1.91 | 89.2 |
| Example 11 | TTBMPP | ROPAC (Rh 30 ppm) | 3 | 198 | 80 | 18 | 1.31 | 88.0 |

TABLE 2

| Classification | Ligand (L) | Transition metal compound (Content of transition metal) | Ligand content (% by weight) | L/Rh (mol/mol) | Reaction temperature (° C.) | Reaction pressure (bar) | n/i-BAL ratio | Syn gas yield (%) |
|---|---|---|---|---|---|---|---|---|
| Comparative Example 1 | TTBMPP | ROPAC (Rh 30 ppm) | 6 | 395 | 80 | 18 | 1.31 | 71.4 |
| Comparative Example 2 | TTBMPP | ROPAC (Rh 400 ppm) | 3 | 15 | 80 | 18 | 2.41 | 91.7 |
| Comparative Example 3 | CHDP | ROPAC (Rh 250 ppm) | 3 | 46 | 90 | 18 | 2.10 | 85.6 |
| | | | | | 80 | | 2.18 | 85.1 |
| | | | | | 75 | | 2.29 | 83.4 |
| | | | | | <75 | | — | 10.1 |
| Comparative Example 4 | TDMPP | ROPAC (Rh 250 ppm) | 3 | 31 | 90 | 18 | 7.77 | 91.2 |
| | | | | | 80 | | 7.87 | 89.1 |
| | | | | | 70 | | 8.24 | 86.9 |
| Comparative Example 5 | TDMPP | ROPAC (Rh 250 ppm) | 6 | 62 | 90 | 8 | 9.97 | 90.8 |
| | | | | | 80 | | 10.15 | 90.1 |
| | | | | | 70 | | 10.45 | 89.4 |
| Reference Example 1 | TTBMPP | ROPAC (Rh 50 ppm) | 11 | 436 | 70 | 18 | 2.10 | 87.9 |
| Reference Example 2 | TTBMPP | ROPAC (Rh 100 ppm) | 1 | 20 | 70 | 18 | 1.56 | 61.9 |
| Reference Example 3 | TTBMPP | ROPAC (Rh 24 ppm) | 3 | 247 | 80 | 18 | 1.42 | 73.2 |

* TTBMPP: tris(2-tert-butyl-4-methylphenyl)phosphite
* CHDP: cyclohexyldiphenylphosphine
* TDMPP: tris(2,4-dimethylphenyl)phosphite As shown in Table 1, when an aldehyde was prepared using the hydroformylation catalyst containing TTBMPP of the present disclosure (Examples 1 to 11), selectivity to isobutyraldehyde and synthesis gas yield were superior to those of Control Example. In particular, within a reaction temperature of 70 to 90° C., a reaction pressure of 9 to 18 bar, a L/Rh molar ratio of 24 to 237, or 3 to 9% by weight of a phosphite ligand, the normal/iso ratio of an aldehyde was lower, and synthesis gas yield was increased.

On the other hand, as shown in Table 2, when different kinds of ligands instead of the TTBMPP ligand according to the present disclosure were used (Comparative Examples 3 to 5), the normal/iso ratio of an aldehyde was very high, and synthesis gas yield was significantly decreased.

In addition, when the content of the transition metal used in the reaction was outside of the range specified herein (Comparative Examples 1 and 2), the normal/iso ratio of an aldehyde was very high, or synthesis gas yield was significantly decreased.

Additional Experimental Example

The catalytic activity and stability of each catalyst composition prepared in Control Example, Examples 1 and 2, Examples 4, and Comparative Examples 3 to 4 were measured by the following method and shown in Table 3.

Measurement Method

Catalytic activity (normal activity, %): The total amount of normal-butyraldehyde and isobutyraldehyde prepared by the reaction (reaction pressure of 8 bar and reaction temperature of 90° C.) according to Control Example was set to 100%, and the total amount of normal-butyraldehyde and isobutyraldehyde prepared according to each of Examples and Comparative Examples was calculated as a percentage by Equation 1 below.

Catalytic activity=(total amount of normal-butyraldehyde and isobutyraldehyde of Example or Comparative Example/total amount of normal-butyraldehyde and isobutyraldehyde of Control Example)×100     [Equation 1]

Catalytic stability (Normal stability, %): After the reaction was performed according to Control Example (reaction pressure of 8 bar and reaction temperature of 90° C.), the amount of propylene gas consumed in the reaction was measured. The catalyst solutions prepared in Examples and Comparative Examples were inactivated at the inactivation temperatures shown in Table 1 below for 15 hours, and then hydroformylation was performed in the same manner (reaction pressure of 8 bar and reaction temperature of 90° C.). Then, the amount of propylene gas consumed in the reaction was measured. The consumption amount of propylene gas before inactivation in Control Example and the consumption amount of propylene gas after inactivation for hours in Control Examples, Examples, or Comparative Examples were compared and calculated as a percentage by Equation 2 below.

Catalytic stability=(consumption amount of propylene gas after inactivation for 15 hours in Control Example, Example, or Comparative Example/consumption amount of propylene gas before inactivation in Control Example)×100     [Equation 2]

As shown in Table 3, it was confirmed that the catalyst compositions of Examples 1, 2, and 4 prepared according to the present disclosure had significantly higher catalytic activity than the catalyst composition of Control Example and maintained high stability even after inactivation. Also, by adjusting the inactivation temperature as described above, it was confirmed that the inactivation temperature of the catalyst composition affected catalytic stability.

On the other hand, in Comparative Example 3 using a phosphine compound as a ligand and Comparative Example 4 using TDMPP as a ligand, it was confirmed that the catalytic activity was very low and the catalytic stability was significantly lowered after inactivation.

Additional Example

Additional Example 1, and Reference Examples 4 and 5

Except that ROPAC and phosphite compounds were added in the amount shown in Table 4 below and reacted at a reaction temperature of 80° C. and a reaction pressure of 18 bar, the reaction was performed in the same manner as in Control Example.

TABLE 3

| Classification | Transition metal compound (Content of transition metal) | Ligand | Ligand content (% by weight) | Catalytic activity (%) | Inactivation temperature (° C.) | Catalytic stability (%) |
|---|---|---|---|---|---|---|
| Control Example | ROPAC (250 ppm) | TPP | 6 | 100 | 120 | 42 |
| Example 1 | ROPAC (50 ppm) | TTBMPP | 3 | 680 | 120<br>100 | 549<br>713 |
| Example 2 | ROPAC (250 ppm) | TTBMPP | 6 | 504 | 120<br>100 | 127<br>330 |
| Example 4 | ROPAC (250 ppm) | TTBMPP | 3 | 812 | 120<br>100 | 107<br>291 |
| Comparative Example 3 | ROPAC (250 ppm) | CHDP | 3 | 115 | 120 | 61 |
| Comparative Example 4 | ROPAC (250 ppm) | TDMPP | 3 | 171 | 120<br>100 | 35<br>110 |

TABLE 4

| Classification | Ligand (L) | Transition metal compound (Content of transition metal) | Ligand content (% by weight) | L/Rh (mol/mol) | Reaction temperature (°C.) | Reaction pressure (bar) | n/i-BAL ratio | Syn gas yield (%) |
|---|---|---|---|---|---|---|---|---|
| Additional Example 1 | TTBMPP | ROPAC (Rh 70 ppm) | 3 | 85 | 80 | 18 | 1.23 | 89.9 |
| Reference Example 4 | TTBMPP | ROPAC (Rh 35 ppm) | 3 | 170 | 80 | 18 | 1.30 | 89.2 |
| Reference Example 5 | TTBMPP | ROPAC (Rh 100 ppm) | 3 | 59 | 80 | 18 | 1.31 | 89.0 |

Additional Experimental Example

The catalytic activity and stability of each of the catalyst compositions prepared in Control Example, Examples 1 and 4, Additional Example 1, and Reference Examples 4 and 5 were measured in the same manner as described above and are shown in Table 5 below.

TABLE 5

| Classification | Transition metal compound (Content of transition metal) | Ligand | Ligand content (% by weight) | Catalytic activity (%) | Inactivation temperature (°C.) | Catalytic stability (%) |
|---|---|---|---|---|---|---|
| Control Example | ROPAC (250 ppm) | TPP | 6 | 100 | 120 | 42 |
| Example 1 | ROPAC (50 ppm) | TTBMPP | 3 | 680 | 120 | 549 |
| Additional Example 1 | ROPAC (70 ppm) | TTBMPP | 3 | 730 | 120 | 510 |
| Example 4 | ROPAC (250 ppm) | TTBMPP | 3 | 812 | 120 | 107 |
| Reference Example 4 | ROPAC (35 ppm) | TTBMPP | 3 | 501 | 120 | 300 |
| Reference Example 5 | ROPAC (100 ppm) | TTBMPP | 3 | 370 | 120 | 273 |

As shown in Table 4, the catalyst compositions prepared in Example 1 and Additional Example 1 according to the present disclosure and the catalyst compositions prepared in Reference Examples 4 and 5 were similar in isoaldehyde selectivity and synthesis gas yield.

On the other hand, as shown in Table 5, in the case of the catalyst compositions prepared in Example 1 and Additional Example 1, even though a small amount of the expensive transition metal of 50 or 70 ppm was used, the catalyst compositions exhibited excellent catalytic activity and stability (catalytic activity of 600% or more and catalytic stability of 500% or more).

Therefore, when hydroformylation of an olefin was performed in the presence of the catalyst containing a specified amount of a TTBMPP ligand at a reaction temperature and reaction pressure within a specified range, the expensive ligand and transition metal compound were used in an appropriate amount, which was desirable in terms of cost and marketability, the catalytic activity and stability of the catalyst was maintained high, and the normal/iso (n/i) ratio of a prepared aldehyde was significantly lowered and synthesis gas yield was dramatically increased.

The invention claimed is:

1. A hydroformylation catalyst, comprising:
a phosphite ligand represented by Formula 1 below; and

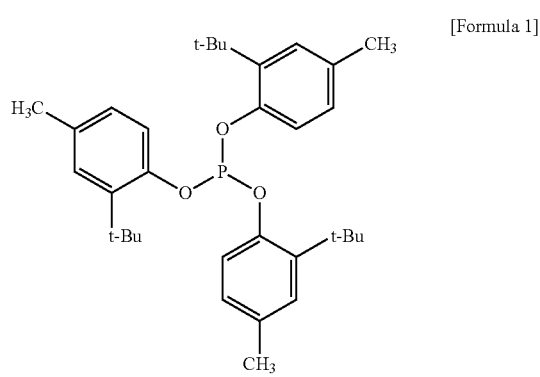

[Formula 1]

a transition metal compound, which is (acetylacetonato)carbonyl(triphenylphosphine)rhodium [Rh(AcAc)(CO)(TPP)], wherein a molar ratio of the phosphite ligand to the transition metal compound (L/M) is 75 to 237.

2. The hydroformylation catalyst according to claim 1, wherein the hydroformylation catalyst catalyzes hydroformylation of propylene to butyraldehyde.

3. The hydroformylation catalyst according to claim 2, wherein a molar ratio of n-butyraldehyde to isobutyraldehyde in the butyraldehyde prepared by catalysis of the hydroformylation catalyst is 2 or less.

4. A method of preparing an aldehyde, comprising a hydroformylation step of reacting an olefin with synthesis gas in the presence of the hydroformylation catalyst according to claim 1 to prepare an aldehyde, wherein the synthesis gas comprises carbon monoxide and hydrogen.

5. The method according to claim 4, wherein a molar ratio of the carbon monoxide to the hydrogen is from 5:95 to 70:30.

6. The method according to claim 4, wherein the hydroformylation step is performed at a reaction temperature of 50 to 90° C. and a reaction pressure of 5 to 25 bar.

7. The method according to claim 4, wherein the hydroformylation step is performed at a reaction temperature of 70 to 90° C. and a reaction pressure of 5 to 13 bar.

8. The method according to claim 4, wherein the hydroformylation step is performed at a reaction temperature of 70 to 90° C. and a reaction pressure of 14 to 20 bar.

9. The method according to claim 4, wherein the olefin is propylene, and the aldehyde is butyraldehyde.

10. The method according to claim 9, wherein a molar ratio of n-butyraldehyde to isobutyraldehyde in the butyraldehyde is 2 or less.

11. The method according to claim 4, wherein synthesis gas yield (syn gas yield) in the hydroformylation step is 80% by weight or more.

* * * * *